United States Patent [19]

Bowers et al.

[11] Patent Number: 4,632,761
[45] Date of Patent: Dec. 30, 1986

[54] CENTRIFUGAL MICROCONCENTRATOR AND METHODS FOR ITS USE

[75] Inventors: William F. Bowers, Topsfield; Peter N. Rigopulos, Boxford, both of Mass.

[73] Assignee: W. R. Grace & Co., New York, N.Y.

[21] Appl. No.: 523,208

[22] Filed: Aug. 15, 1983

[51] Int. Cl.[4] .............................................. B01D 13/00
[52] U.S. Cl. .................................... 210/650; 210/781; 210/380.1; 210/407
[58] Field of Search ..................... 494/36; 55/301, 429; 210/380.1, 369, 650, 407, 768, 781, 359, 927; 435/14

[56] References Cited

U.S. PATENT DOCUMENTS

| | | | |
|---|---|---|---|
| 815,363 | 3/1906 | Ter Meer | 210/477 |
| 2,775,350 | 12/1956 | Jones | 210/157 |
| 2,854,143 | 9/1958 | Novak | 210/335 |
| 3,356,219 | 12/1967 | Muller | 210/407 X |
| 3,386,585 | 6/1968 | Weyland et al. | 210/445 |
| 3,471,019 | 10/1969 | Transen et al. | 210/94 |
| 3,488,768 | 1/1970 | Rigopulos | 210/23 |
| 3,583,627 | 6/1971 | Wilson | 233/2 |
| 3,608,736 | 9/1971 | Wong | 210/477 |
| 3,682,321 | 8/1972 | Smith | 210/477 |
| 3,817,379 | 6/1974 | Zipilivan et al. | 210/94 |
| 4,017,396 | 4/1977 | Skau | 210/232 |
| 4,066,512 | 1/1978 | Lai et al. | 435/14 X |
| 4,162,979 | 7/1979 | Wahlefeld et al. | 210/282 |

OTHER PUBLICATIONS

Amicon Publication 472–Separate Free from Protein–Bound Microsolute, 1978.
Amicon Publication 460C–Micropartition System MPS-1, 1981.
Amicon Publication 439A–Minicon ® Concentrators for Rapid Enrichment of Biological Solutions, 1969.
Amicon Publication 441D–Centriflo ® Membrane Ultrafiltration by Centrifugation, 1981.

Primary Examiner—Frank Spear
Attorney, Agent, or Firm—Stacey L. Channing; William L. Baker

[57] ABSTRACT

Disclosed is a centrifugal microconcentrator and methods for using the microconcentrator to concentrate macromolecules from a solution without filtering to dryness and to centrifugally recover a maximal amount of concentrated macromolecular retentate.

66 Claims, 7 Drawing Figures

CENTRIFUGAL MICROCONCENTRATOR AND METHODS FOR ITS USE

BACKGROUND OF THE INVENTION

This invention relates to centrifugal methods and devices for concentrating macromolecules from a solution without filtering to dryness and for recovering a maximal amount of concentrated macromolecular retentate.

There have been a number of analytical procedures developed in the biochemical art wherein it is required to remove solvent from protein solutions in order to have a more concentrated protein sample which can be analyzed effectively, or in order to have a protein-free filtrate for analysis, or to replace or remove low molecular weight ions or solutes, or to study protein-binding attributes of various chemicals in combination with various protein samples. Many other analytical procedures, involving not only proteins but macromolecular species in general, have also been developed wherein it is necessary to concentrate a macromolecular component in a liquid sample.

When concentrating small volumes of macromolecules in solution using filtration e.g., ultrafiltration, there exists the problem of filtration to dryness. Although a fixed volume of buffer may be added to a microvolume concentration device to redissolve macromolecules retained after filtration to dryness, it is generally found that total mass recovery of macromolecules is significantly less, and biological activity recovery is often reduced, as compared to the case when filtration is stopped at the desired final retentate volume.

In the prior art, the Amicon Minicon ® adsorbent activated concentrator is provided with an impermeable seal coating on the portion of the membrane in contact with the desired final retentate volume. This coating impedes filtration to dryness, but does not prevent it, due to wicking caused by surface tension forces, which allows continued filtration after the retentate meniscus recedes onto the coated area.

The centrifugal microconcentrator of this invention is of similar design to the Amicon MPS-1 Micropartition System (Publication 472). In the MPS-1, however, the membrane support is provided with filtrate ducts under all portions of the membrane, so that if left unattended while being centrifuged in a fixed angle rotor, the MPS-1 will filter to dryness.

Besides the problem of filtration to dryness, there also exists the problem of recovery of microvolumes of concentrated macromolecular retentate from a microconcentrator. Recovery with a conventional pipette is difficult due to film losses caused by surface tension wetting of the membrane and reservoir walls. Also, the pipette tip may damage the membrane skin, preventing optional reuse of the microconcentrator. For example, recovery of retentate with a pipette from the centrifugal self-cleaning ultrafilter, described in U.S. Pat. No. 3,488,768, the teachings of which are incorporated herein, is limited due to the large membrane surface area which causes adsorptive and film loss of the macromolecules.

Accordingly, it is a principal object of this invention to provide a centrifugal microconcentrator which can concentrate macromolecules from a solution without filtering to dryness.

It is another object of this invention to provide such a microconcentrator which gives constant final retentate volume, for a given fixed rotor angle, regardless of the alignment of the device in the rotor.

It is another object of this invention to use such a concentrator in a centrifugal recovery process in which a maximal amount of concentrated macromolecular retentate is obtained without damage to the membrane and with minimal film loss.

It is another object of this invention to provide a centrifugal recovery process for the recovery of a maximal amount of concentrated macromolecular retentate from a centrifugal concentrator device.

It is a further object of this invention to provide a reuseable centrifugal microconcentrator.

It is a still further object of this invention to provide a centrifugal microvolume concentrator that is economic to manufacture.

SUMMARY OF THE INVENTION

The problems of the prior art are overcome by the provision of a centrifugal microconcentrator device in a novel centrifugal filtration system and methods for use of a microconcentrator device to concentrate macromolecules from a solution without filtering to dryness and/or to centrifugally recover a maximal amount of concentrated macromolecular retentate.

The centrifugal filtration system of the invention for the concentration of macromolecules from a solution comprises:

(a) a novel microconcentrator device comprising:
 (1) a sample reservoir;
 (2) a filtrate cup situated below the sample reservoir;
 (3) a filter means separating the sample reservoir from the filtrate cup, said filter means comprising:
  (a) a semipermeable membrane; and
  (b) a support for said membrane, said support having one or more filtrate ducts to allow for passage of filtrate from the membrane into the filtrate cup, said filtrate duct or ducts being offset sufficiently inward from the edge of the membrane, so that when the apparatus is used in a fixed angle centrifuge rotor, filtration stops and a concentrated macromolecular final retentate volume is obtained once the retentate meniscus reaches the centrifugal radial level of the outermost edge of the outermost filtrate duct;
 (4) means for providing a liquid tight seal between the periphery of the sample reservoir, the membrane, and the membrane support;
 (5) means for attaching the filter means to the filtrate cup.
 (6) means for attaching the sample reservoir to the filter means; and
(b) a fixed angle centrifuge rotor to receive said microconcentrator device.

In a preferred form, the centrifugal filtration system is an ultrafiltration system and the membrane employed is an anisotropic ultrafiltration membrane characterized by a maximum pore size of 500 millimicrons. The filtrate ducts in the membrane support are preferably located in axial symmetry with respect to the longitudinal axis of the microconcentration device, said filtrate ducts most preferably comprising a series of discontinuous arcs defining an annular slot. The preferred filtration system further comprises an O-ring for providing a liquid tight seal between the periphery of the sample reservoir, the membrane, and the membrane support and a vented retentate cup for closing the sample reservoir.

In the method of the invention for concentrating macromolecules from a solution without filtering to dryness, the sample reservoir of the above-described novel microconcentrator device is filled with a macromolecular solution; the microconcentrator device is placed in a fixed angle centrifuge rotor so that during centrifugation the centrifugal force vector is always at an angle to the membrane surface; and a concentrated macromolecular final retentate volume is obtained by centrifuging the microconcentrator device until the retentate meniscus reaches the centrifugal radial level of the outermost edge of the outermost filtrate duct and filtration stops.

In the preferred method for concentration of macromolecules, after the sample reservoir is filled with a macromolecular solution, it is capped with a vented retentate cup. Also, in the preferred method, the above described preferred microconcentrator device is employed.

The retentate obtained by the preferred method for concentration of macromolecules is preferably recovered by removing the filtrate cup containing filtrate from the microconcentration device; inverting the device so that the retentate cup is situated below the sample reservoir, and centrifuging the apparatus in the inverted orientation to expel a maximal amount of retentate into the retentate cup. More preferably, before the microconcentrator device is centrifuged, the retentate cup is inserted partially into the filtrate cup in such a manner that it forms an airtight seal preventing filtrate evaporation.

The invention further provides a system solely for the centrifugal recovery of concentrated macromolecular retentate comprising:
(a) an apparatus comprising:
(1) a retentate reservoir containing macromolecular retentate;
(2) a filter means attached to the top of the retentate reservoir, said filter means comprising:
 (a) a semipermeable membrane; and
 (b) an inverted support for said membrane having one or more filtrate ducts, which, in conjunction with sealing means, holds the membrane in place;
(3) means for providing a liquid tight seal between the periphery of the retentate reservoir, the membrane, and the membrane support;
(4) retentate cup attached to the bottom of the retentate reservoir;
(5) means for attaching the filter means to the retentate reservoir;
(6) means for attaching the retentate cup to the retentate reservoir; and
(b) a centrifuge to receive said apparatus.

In a preferred form, the membrane of the apparatus of the recovery system comprises an anisotropic ultrafiltration membrane.

In the method of the invention for centrifugally recovering concentrated macromolecular retentate from the retentate reservoir of the above-described recovery apparatus, the apparatus is centrifuged to expel a maximal amount of retentate into the retentate cup.

BRIEF DESCRIPTION OF THE DRAWING

FIG. 2b is a cross-sectional view taken along line A—A of FIG. 2a.

DESCRIPTION OF THE PREFERRED EMBODIMENT

Figure 1:
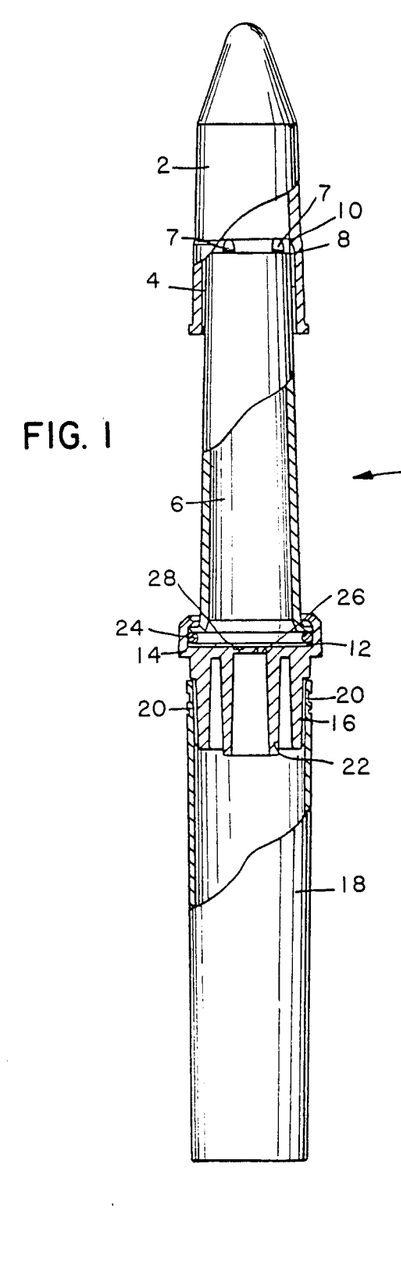
FIG. 1 is a schematic view in partial cross-section of a microconcentrator device of the invention in concentration mode.

Referring to FIG. 1, there is shown a preferred form of the microconcentrator device of the invention 1 comprising a retentate cup 2 which has a venting rib 4, said venting rib 4 preferably being one of three venting ribs molded into the inside surface of the retentate cup and designed to engage the outside surface of the sample reservoir 6. Stop means 7 are also molded into the inner surface of the retentate cup. The venting ribs together with the stop means serve to prevent air locking when the sample reservoir is capped with the retentate cup during centrifugation. Although this is one way of venting the retentate cup to prevent air locking, any way that accomplishes the same result will do, e.g., the retentate cup can fit over ribs molded into the outer surface of the sample reservoir.

Figure 3:
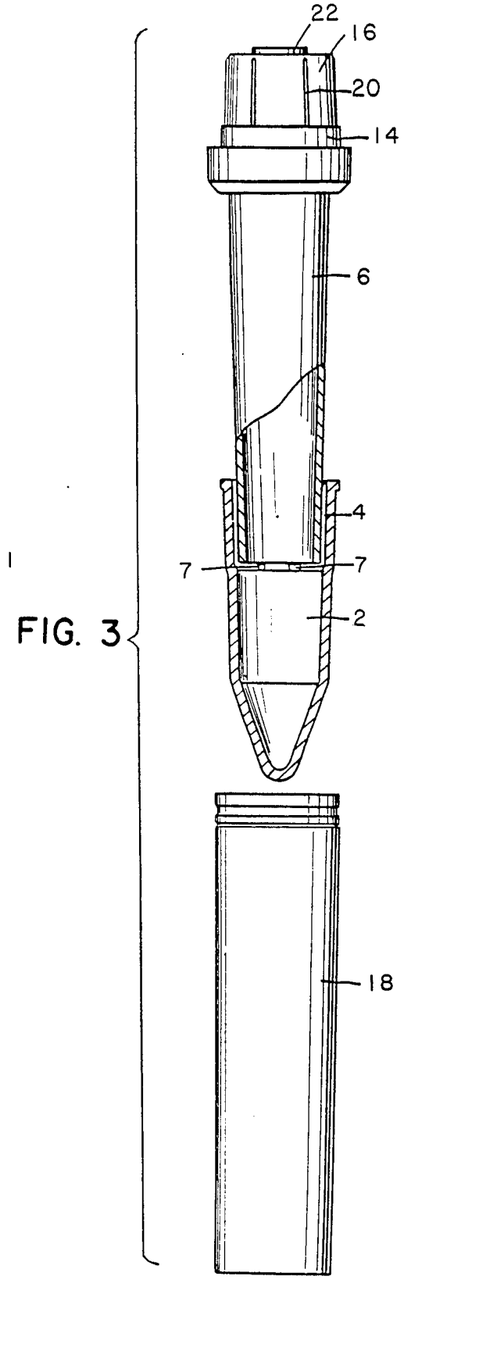
FIG. 3 is a schematic view in partial cross-section of a microconcentrator device of the invention in recovery mode.

The microconcentrator device of the invention is preferably capped during concentration in order to prevent sample evaporation. The cap used is preferably vented to prevent airlocking from occurring. The cap used also preferably comprises a retentate cup adapted to receive macromolecular retentate when the microconcentrator device of the invention is in recovery mode as seen in FIG. 3.

Figure 2A:
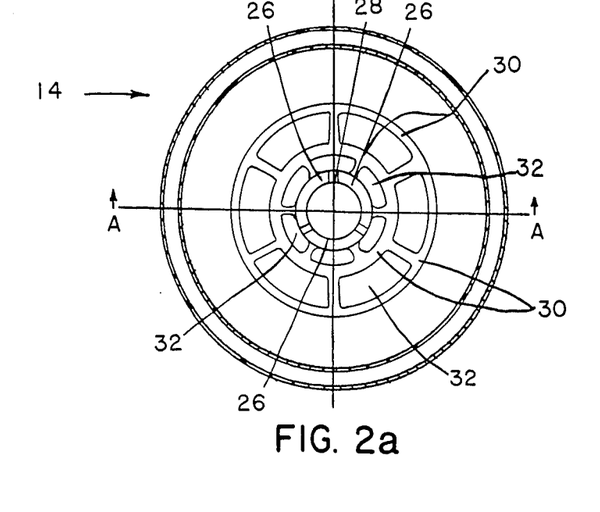
FIG. 2a is a top view of the membrane support used in the microconcentrator device of FIG. 1.
Figure 2B:
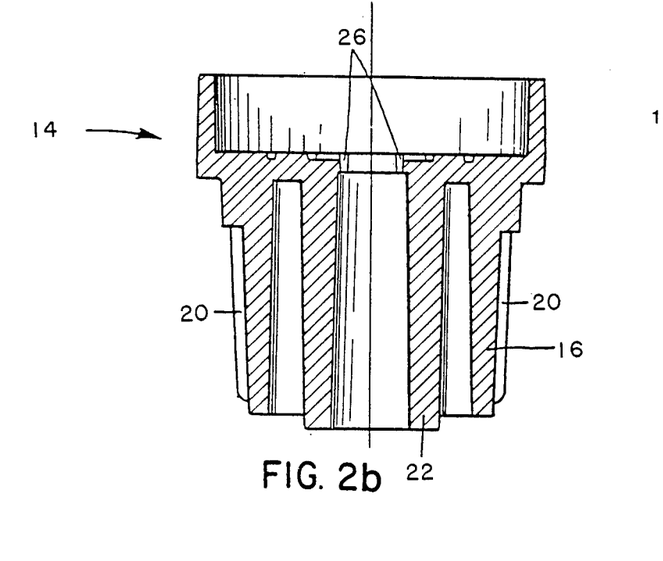

The microconcentrator device further comprises a filter means comprising a semipermeable membrane 12 and a membrane support 14 shown more clearly in FIGS. 2a and 2b. The sample reservoir 6 is attached to the filter means by crimping of the membrane support 14 over the sample reservoir 6. Any means for attaching the sample reservoir to the filter means will do. If the sample reservoir is attached to the filter means by crimping, then the membrane cannot be replaced if it becomes defective. However, if the sample reservoir is attached to the filter means, for example, by a pair of removable clips, then the membrane may be easily replaced for subsequent reuse of the microconcentrator if desired.

As seen in FIGS. 1 and 2, the preferred membrane support 14 has a filtrate cup engagement skirt 16 for engagement of the membrane support 14 with the filtrate cup 18. The membrane support 14 has venting ribs 20, said venting ribs 20 being two of six ribs molded into the outside surface of the engagement skirt 16 that the filtrate cup fits over. The membrane support 14 also has a filtrate sleeve 22, which together with the venting ribs 20, prevent air locking between the filtrate cup engagement skirt 16 and the filtrate cup 18.

An O-Ring 24 provides a liquid tight seal between the periphery of the sample reservoir 6, the membrane support 14 and the membrane 12. Any means for sealing may be used so long as the membrane is completely sealed about its periphery.

Although any type of semipermeable membrane may be used in the microconcentrator device of the invention, anisotropic membranes, i.e. membranes having an extremely thin microporous barrier layer and a relatively thick macroporous support layer are preferred and anisotropic ultrafiltration membranes characterized by a maximum pore size of 500 millimicrons are more preferred.

Membrane support 14 of FIG. 1 is more clearly shown in FIGS. 2a and 2b. As seen in FIG. 2a, the membrane support 14 has a flat grid surface supporting the membrane yet permitting a high rate of flow. The membrane support 14 has filtrate ducts comprising three discontinuous arcs 26 defining an annular slot, which arcs 26 allow for passage of filtrate from the membrane 12 into the filtrate cup 18. The three discontinous arcs 26 are located in axial symmetry with respect to the longitudinal axis of the microconcentrator device. The three arcs 26 are separated from each other by 3 supporting tabs 28. The membrane support 14 has collection grooves 30 leading to the arcs 26 which enable filtrate to flow through the membrane support at a greater speed. The membrane support 14 also has lands 32 for support of the membrane.

Figure 4A:
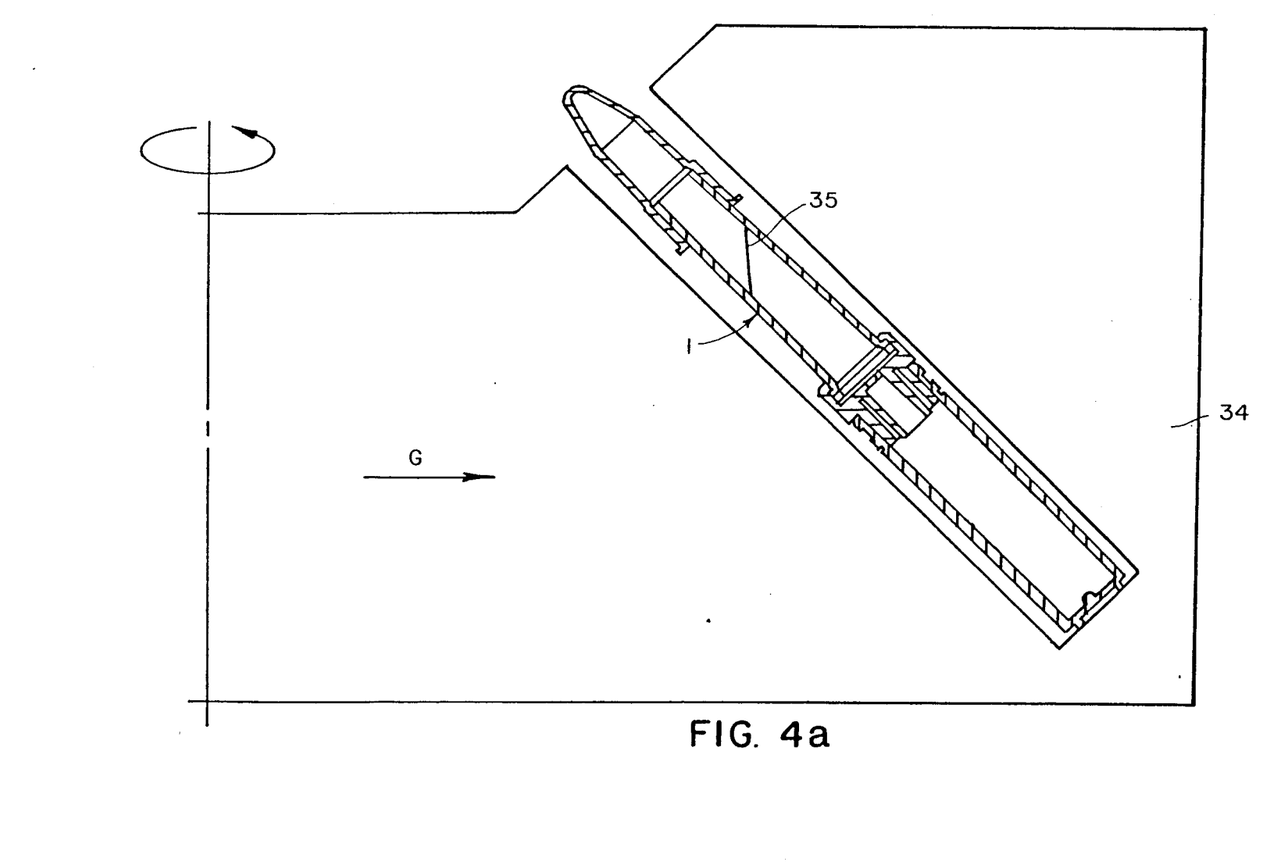
FIG. 4a is a functional schematic view in partial cross-section of a microconcentrator device of the invention positioned in a fixed angle rotor at the beginning of the concentration cycle.
Figure 4B:
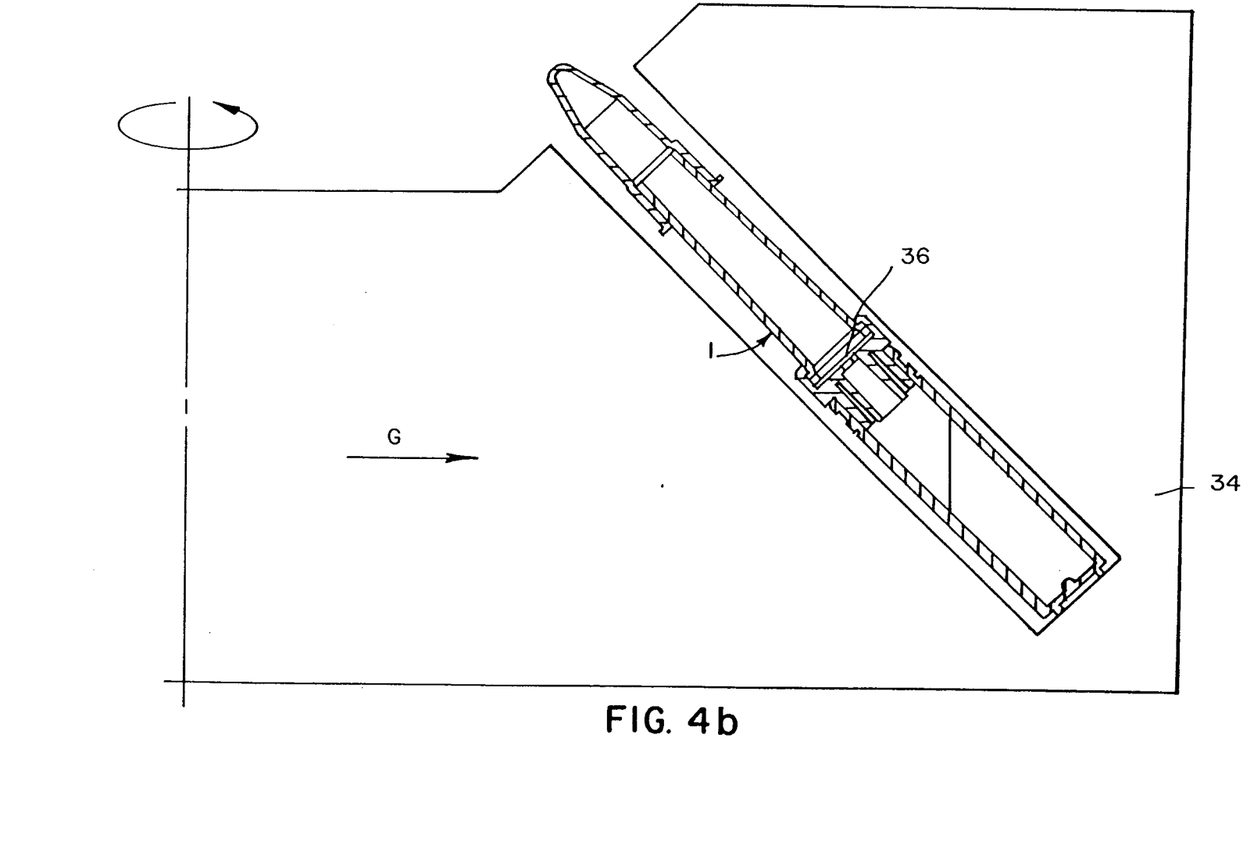
FIG. 4b is a functional schematic view in partial cross-section of a microconcentrator device of the invention positioned in a fixed angle rotor at the end of the concentration cycle when equilibrium is reached.

Any system of filtrate ducts may be employed in the membrane support, e.g. a sole filtrate duct comprising a circular opening, so long as the membrane support has one or more filtrate ducts, and said filtrate duct or ducts are offset sufficiently inward from the edge of the membrane, so that when the apparatus is used in a fixed angle centrifuge rotor 34 as shown in FIG. 4, equilibrium is achieved and filtration stops once the retentate meniscus reaches the centrifugal radial level of the outermost edge of the outermost filtrate duct, due to counterbalancing hydrostatic pressure of filtrate between the membrane and membrane support. There is no possibility of filtration to dryness, even with extended centrifugation needed to allow for variation in individual membrane filtration rates.

The filtrate duct or ducts of the membrane support are preferably located such that when the apparatus is used in a fixed angle centrifuge rotor, the distance from the outermost edge of the outermost filtrate duct to the centrifugal wall of the sample reservoir is essentially nonvariant with regard to alignment of the apparatus in the rotor. Thus, for a given rotor angle, a constant final volume is obtained regardless of the alignment of the device in the rotor. The final volume can be varied by selection of readily available centrifuge rotors of differing angles, generally in the range of 26°-55°, with the most common rotor angles being 45° or 34°. If the preferred device in FIGS. 1 and 2 is used, the final retentate volume obtained using a 34° rotor angle is approximately 50 microliters, while the final retentate volume obtained using a 45° rotor angle is approximately 25-30 microliters.

If the filtrate duct or ducts are asymmetric, that is, if when the apparatus is used in a fixed angle centrifuge rotor, the distance from the outermost edge of the outermost filtrate duct to the centrifugal wall of the sample reservoir varies with regard to alignment of the apparatus in the rotor, then means, such as a tab positioned on the edge of the membrane support, are necessary in order to axially align the apparatus in the fixed angle rotor. In this case, not only may final retentate volumes be varied using the same device by selection of centrifuge rotors of differing angles, but they may also be varied by variation of the axial alignment of the apparatus in the fixed angle rotor.

The retentate cup 2, the sample reservoir 6, the membrane support 14 and the filtrate cup 18 are preferably injection molded of plastic, and are of such low cost that the microconcentrator is disposable after one use.

Referring to FIG. 4a, after the sample reservoir 6 of the microconcentrator device 1 is filled with macromolecular solution to sample meniscus level 35, device 1 is centrifuged in a fixed angle centrifuge rotor 34 at a relatively high speed (e.g. 1000–5000×g) until the retentate meniscus 36 reaches the centrifugal radial level of the outermost edge of the outermost filtrate duct as shown in FIG. 4b and filtration stops. After filtration stops and final retentate volume is obtained, the retentate is recovered by use of the microconcentrator in recovery mode as shown in FIG. 3.

In order for the microconcentrator to be in recovery mode as depicted in FIG. 3, the filtrate cup 18 containing the filtrate is removed from the microconcentrator and the microconcentrator is inverted so that the retentate cup 2 is situated below the sample reservoir 6. The apparatus is then centrifuged briefly, generally less than 5 minutes, at a low speed (e.g. 1000–1500×g) in the inverted orientation to expel a maximal amount of retentate into the retentate cup. The apparatus may be centrifuged in a fixed angle rotor or a swinging bucket rotor. The centrifugal force causes a nearly quantitative transfer of solution into the retentate cup 2, overcoming the effect of surface tension which otherwise causes adherence of solution to the membrane and reservoir walls of the apparatus. For any retentate volume obtained by concentration that is greater than 20 microliters, the inverted microconcentrator can recover at least 90% of the macromolecular mass in the retentate. If a greater percent recovery is desired, buffer may be added to the sample reservoir and the apparatus can be centrifuged again in the inverted orientation shown in FIG. 3.

Figure 5:
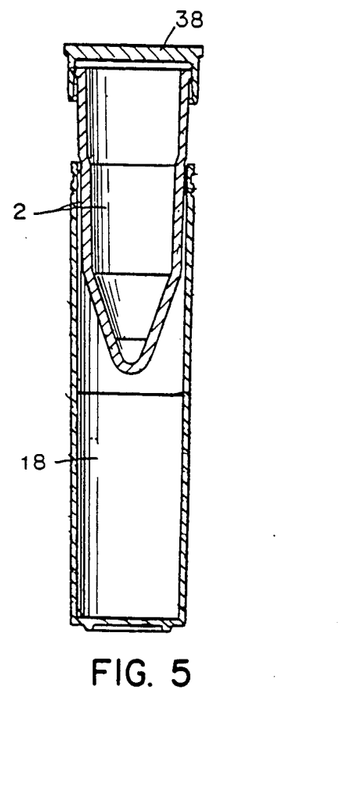
FIG. 5 is a schematic view in partial cross-section of the capped retentate cup inserted into the filtrate cup for storage after removal of the rest of the microconcentrator device.

Before centrifugation of the inverted device, the retentate cup 2 is preferably inserted partially into the filtrate cup 18 in such a manner that it forms an airtight seal. Although the airtight seal is not necessary for recovery, the airtight seal serves to prevent filtrate evaporation during storage. After centrifugation, the sample reservoir 16 is removed from the retentate cup 2 and the retentate cup 2, which is partially inserted into the filtrate cup 18, is capped with cap 38 as shown in FIG. 5 for storage. If desired, the retentate cup can be partially inserted into the filtrate cup and capped for storage after the sample reservoir is removed from the retentate cup.

The invention is further illustrated by the following non-limiting examples.

EXAMPLE 1

Four microconcentrator devices of the invention containing Amicon YMT membranes (standard Amicon anisotropic ultrafiltration membranes with a nominal molecular weight cutoff of 30,000 Daltons) and containing the preferred membrane support depicted in FIG. 2 were assembled as shown in FIG. 1 and the sample reservoirs were filled with 1 ml of a 1 mg/ml solution of bovine serum albumin (BSA). The loaded devices were inserted into a 45° fixed angle rotor and centrifuged for 40 minutes at 3500 rpm in an LEC model number PR-J centrifuge. After centrifugation, the filtrate cups were removed from the devices, the devices inverted, and the devices then reinserted into their corresponding filtrate cups in the inverted position as shown in FIG. 3. The devices were placed back into the above centrifuge rotor and centrifuge and spun at 1500 rpm for 2 minutes to quantitatively transfer the retentate into the retentate cup.

Ultraviolet absorption at a wavelength of 280 nm was employed for detecting protein in the retentate. All volumes were measured gravimetrically. The % BSA in the retentate was calculated as follows:

% BSA retentate =

$$\left( \frac{A_{280} \text{ retentate} \times \text{volume retentate}}{A_{280} \text{ 1 mg/ml } BSA \times \text{volume of solution}} \right) \times 100$$
$$\text{solution loaded into devices} \quad \text{added to devices}$$

The amount of protein in the ultrafiltrate was determined by adding 5.0 ml of Bio-Rad Protein Assay Dye Concentrate (Bio-Rad catalogue number 500-0006) to 0.1 ml of the filtrate and measuring the absorbance of the resulting solution at 595 nm. Concentration of protein in the filtrate was interpolated directly from a standard curve of $A_{595}$ vs concentration generated by the above technique with standards containing 2.0%, 1.07% and 0.5% BSA.

Results indicated that an average of 96.0% of the bovine serum albumin loaded into the devices was recovered in the retentate from an average retentate volume of 0.035 ml. No protein was detected in the ultrafiltrates.

EXAMPLE 2

8 microconcentrator devices were assembled as in Example 1 except that there were no caps for the devices and early prototype membrane supports having one central filtrate duct were used. Male urine (negative for human chorionic gonadotropin (HCG)) was filtered through Whatman #1 filter-paper, obtained from the Whatman company, and spiked with HCG (Calbiochem catalogue number 869029) at levels of 5, 7.5, 10, and 15 milliinternational units/ml (mIU/ml) of urine. 1 ml of the spiked urine at each level was added to the sample reservoirs of duplicate assembled microconcentrator devices. The loaded devices were centrifuged for 30 minutes at 3800 rpm in a 35° angle head rotor in a Damon/LEC contrifuge model HN-SII resulting in approximately 20 fold reduction in retentate volume.

After centrifugation, the filtrate cups were removed from the devices, the devices were briefly vortex mixed and the devices were inverted into B-Neocept reagent tubes (obtained from Organon Diagnostics). The B-Neocept reagent tubes containing the inverted devices were inserted into the above rotor and centrifuge and spun for 5 minutes at 1000 rpm to transfer the retentate into the B-Neocept tubes.

The B-Neocept tubes were removed from the microconcentrator devices, shaken briefly to mix the retentate with the dried reagents, and placed into the mirrored tube rank supplied with the B-Neocept test kit. Unconcentrated controls were spiked with HCG at levels of 50, 100, 150, 200, 250 and 300 mIU/ml of urine. 0.05 ml of the spiked urine at each level was added to B-Neocept tubes with a pipette. 0.3 ml HEPES buffer supplied with the B-Neocept kit was added to each B-Neocept tube and the tubes were briefly vortexed. The tubes were left undisturbed for 1 hour and read according to the manufacturer's instructions. A positive test (+) was indicated by the appearance of a reddish brown ring in the bottom of the tube while a negative test produced a diffuse sediment in the bottom of the tube (−). An irregular or broken ring was classified as indeterminate and labeled +/−.

| Device | HCG (mIU/ml urine) | Membrane | B-Neocept Assay Result |
|---|---|---|---|
| 1,2 | 5 | YMT | − |
| 3,4 | 7.5 | YMT | +/− |
| 5,6 | 10 | YMT | +/− |
| 7,8 | 15 | YMT | + |
| unconcentrated controls | 50 | — | — |
| | 100 | — | — |
| | 150 | — | +/− |
| | 200 | — | +/− |
| | 250 | — | +/− |
| | 300 | — | + |

These results show an approximately 20× in increase in HCG titer achieved by a 20× concentration in the device. This experiment specifically demonstrates that the microconcentrator devices of this invention can be used to increase the sensitivity of the B-Neocept test. The results of this experiment can be generalized to indicate that biological fluids may be quantitatively concentrated (with greater than 90% recovery) before performing an immunological assay in order to lower detection limits for the antigen.

EXAMPLE 3

6 microconcentrator devices were assembled as in Example 1 except that the membrane supports used contained a single circular 0.5 mm filtrate duct offset slightly from the center of the membrane support and a tab was positioned on the edge of the membrane support for directional orientation. 1 ml of a 1 mg/ml solution of BSA was loaded into each device.

Three devices were placed into a 35° angle head rotor in a Damon/LEC contrifuge model HN-SII with the tab oriented outboard, and three devices were placed into the rotor with the tab 90° clockwise from outboard. The devices were spun at 3500 rpm for one hour. After centrifugation, the devices were removed from the filtrate cups, inverted, and inserted into their corresponding filtrate cups in the inverted position as shown in FIG. 3. The devices were returned to the above centrifuge and rotor and spun at 1500 rpm for 2 minutes to transfer the retentate into the retentate cup. Volume and protein recovered were measured as in Example 1.

Average retentate volume for the devices with the tab outboard was 0.0971 ml, with an average of 96.7% of the BSA recovered in the retentate and none found in the filtrate. Devices with the tab oriented 90° clockwise from outboard produced an average retentate volume of 0.0777 ml, with 94.7% of the BSA recovered in the retentate and none found in the filtrate.

This experiment demonstrates that retentate volumes can be controlled by using a membrane support having the filtrate duct or ducts positioned asymmetrically in the support and then changing the orientation of the membrane support in the rotor.

EXAMPLE 4

Six microcentrator devices were assembled as in Example 1 except that Amicon type YC05 membranes (standard Amicon anisotropic ultrafiltration membranes with a molecular weight cutoff of 1000 Daltons) were used. 1 ml of a 0.02% solution of vitamin B (Sigma catalogue number V2876) was loaded into the sample reservoir of each device.

The filled devices were spun as in Example 1 except that the centrifugal speed was 5500 rpm and the time of centrifugation was 95 minutes. Retentates were recovered as in Example 1.

Absorption at 570 nm was used for the detection of the vitamin in both the filtrate and the retentate. All volumes were determined gravimetrically.

Calculations were as follows:

$$\text{retentate retenate} = \frac{A_{570} \text{ retentate} \times \text{volume retentate}}{A_{570} \, 0.02\% \, B12 \times \text{volume loaded into devices}} \times 100$$

$$\% \text{ filtrate} = \frac{A_{570} \text{ filtrate} \times \text{volume filtrate}}{A_{570} \, 0.02\% \, B12 \times \text{volume loaded into devices}} \times 100$$

Five of the six devices passed less than 3.0% of the vitamin B 12 into the filtrate, with greater than 95% recovered in the retentate. In the sixth unit, only 59.7% of the B 12 was recovered in the retentate, with 41.4% found in the filtrate. The results of the final device are indicative of a membrane or seal failure. The sample, however, is easily recovered and reconcentrated using another device.

Although this invention has been described with reference to its preferred embodiments, other embodiments can achieve the same results. Variations and modifications to the present invention will be obvious to those skilled in the art and it is intended to cover in the appended claims all such modifications and equivalents that follow in the true spirit and scope of this invention.

It is claimed:

1. A centrifugal filtration apparatus for the concentration of macromolecules from a solution comprising:
   a sample reservoir;
   a filtrate cup situated below the sample reservoir;
   a filter means separating the sample reservoir from the filtrate cup, said filter means comprising:
      a semipermeable membrane; and
      a support for said membrane, said support having one or more filtrate ducts to allow for passage of filtrate from the membrane into the filtrate cup, said filtrate duct or ducts being located such that when the apparatus is used in a fixed angle centrifuge rotor, the distance from the outermost edge of the outermost filtrate duct to the centrifugal wall of the sample reservoir is essentially nonvariant with regard to alignment of the apparatus in the rotor and said filtrate duct or ducts being offset sufficiently inward from the edge of the membrane to enable filtration to stop and a concentrated macromolecular final retentate volume to be obtained when the apparatus is used in a fixed angle centrifuge rotor and the retentate meniscus reaches the centrifugal radial level of the outermost edge of the outermost filtrate duct;
   means for providing a liquid tight seal between the periphery of the sample reservoir, the membrane, and the membrane support;
   means for attaching the filter means to the filtrate cup; and means for attaching the sample reservoir to the filter means.

2. The filtration apparatus of claim 1 wherein the membrane comprises an anisotropic ultrafiltration membrane.

3. The filtration apparatus of claim 1 wherein the filtrate ducts comprise a series of discontinuous arcs defining an annular slot.

4. The filtration apparatus of claim 1 wherein the apparatus further comprises a cap for closing the sample reservoir.

5. The filtration apparatus of claim 4 wherein the cap comprises a retentate cup adapted to receive macromolecular retentate when the filtrate cup is removed, the apparatus is inverted so that the retentate cup is situated below the sample reservoir, and the apparatus is centrifuged.

6. The filtration apparatus of claim 5 wherein the retentate cup is vented to prevent air locking.

7. The filtration apparatus of claim 1 wherein the membrane support has collection grooves leading to the one or more filtrate ducts which enables the filtrate to flow through the membrane support at a greater speed.

8. A centrifugal system for the concentration of macromolecules from a solution comprising:
   (a) an apparatus comprising:
      a sample reservoir;
      a filtrate cup situated below the sample reservoir;
      a filter means separating the sample reservoir from the filtrate cup, said filter means comprising:
         a semipermeable membrane; and
         a support for said membrane, said support having one or more filtrate ducts to allow for passage of filtrate from the membrane into the filtrate cup, said filtrate duct or ducts being located such that when the apparatus is used in a fixed angle centrifuge rotor, the distance from the outermost edge of the outermost filtrate duct to the centrifugal wall of the sample reservoir is essentially nonvariant with regard to alignment of the apparatus in the rotor and said filtrate duct or ducts being offset sufficiently inward from the edge of the membrane to enable filtration to stop and a concentrated macromolecular final retentate volume to be obtained when the apparatus is used in a fixed angle centrifuge rotor and the retentate meniscus reaches the centrifugal radial level of the outermost edge of the outermost filtrate duct;
      means for providing a liquid tight seal between the periphery of the sample reservoir, the membrane, and the membrane support;
      means for attaching the filter means to the filtrate cup;
      means for attaching the sample reservoir to the filter means; and
   (b) a fixed angle centrifuge rotor to receive said apparatus.

9. The filtration system of claim 8 wherein the membrane comprises an anisotropic membrane.

10. The filtration system of claim 9 wherein the membrane comprises an ultrafiltration membrane.

11. The filtration system of claim 10 wherein the membrane is characterized by a maximum pore size of 500 millimicrons.

12. The filtration system of claim 8 wherein the filtrate duct comprises a single circular opening.

13. The filtration system of claim 8 wherein the filtrate ducts comprise a series of dicontinuous arcs defining an annular slot.

14. The filtration system of claim 8 wherein the means for providing a liquid tight seal between the periphery of the sample reservoir, the membrane, and the membrane support comprises an O-ring.

15. The filtration system of claim 8 wherein the apparatus further comprises a cap for closing the sample reservoir.

16. The filtration system of claim 19 wherein the cap is vented to prevent air locking.

17. The filtration system of claim 15 wherein the cap comprises a retentate cup adapted to receive macromolecular retentate when the filtrate cup is removed, the apparatus is inverted so that the retentate cup is situated below the sample reservoir, and the apparatus is centrifuged.

18. The filtration system of claim 17 wherein the retentate cup is vented to prevent air locking.

19. The filtration system of claim 18 wherein the retentate cup has ribs molded into its inside surface which are designed to engage the outside surface of the sample reservoir.

20. The filtration system of claim 18 wherein the retentate cup has stop means molded into its inner surface.

21. The filtration system of claim 8 wherein the membrane support has collection grooves leading to the one or more filtrate ducts which enable the filtrate to flow through the membrane support at a greater speed.

22. A method for concentrating macromolecules from a solution without filtering to dryness comprising:
   (a) filling the sample reservoir of an apparatus with a macromolecular solution, said apparatus comprising:
   a sample reservoir;
   a filtrate cup situated below the sample reservoir;
   a filter means separating the sample reservoir from the filtrate cup, said filter means comprising:
      a semipermeable membrane; and
      a support for said membrane, said support having one or more filtrate ducts to allow for passage of filtrate from the membrane into the filtrate cup, said filtrate duct or ducts being offset sufficiently inward from the edge of the membrane to enable filtration to stop and a concentrated macromolecular final retentate volume to be obtained when the apparatus is used in a fixed angle centrifuge rotor and the retentate meniscus reaches the centrifugal radial level of the outermost edge of the outermost filtrate duct;
   means for providing a liquid tight seal between the periphery of the sample reservoir, the membrane, and the membrane support;
   means for attaching the filter means to the filtrate cup; and
   means for attaching the sample reservoir to the filter means;
   (b) placing the apparatus in a fixed angle centrifuge rotor so that during centrifugation the centrifugal force vector is always at an angle to the membrane surface; and
   (c) obtaining a concentrated macromolecular final retentate volume by centrifuging the apparatus until the retentate meniscus reaches the centrifugal radial level of the outermost edge of the outermost filtrate duct and filtration stops.

23. The method of claim 22 wherein the membrane comprises an anisotropic membrane.

24. The method of claim 23 wherein the membrane comprises an ultrafiltration membrane.

25. The method of claim 24 wherein the membrane is characterized by a maximum pore size of 500 millimicrons.

26. The method of claim 22 wherein in step b, the apparatus is axially aligned in the fixed angle centrifuge rotor.

27. The method of claim 22 wherein the filtrate duct or ducts are located such that the distance from the outermost edge of the outermost filtrate duct to the centrifugal wall of the sample reservoir is essentially nonvariant with regard to alignment of the apparatus in the rotor.

28. The method of claim 27 wherein the filtrate duct comprises a single circular opening.

29. The method of claim 27 wherein the filtrate ducts comprise a series of discontinuous arcs defining an annular slot.

30. The method of claim 22 wherein the membrane support has collection grooves leading to the one or more filtrate ducts which enable the filtrate to flow through the membrane support at a greater speed.

31. The method of claim 22 wherein the means for providing a liquid tight seal between the periphery of the sample reservoir, the membrane, and the membrane support comprises an O-ring.

32. The method of claim 22 wherein after the sample reservoir is filled with a macromolecular solution in step a, the sample reservoir is capped.

33. The method of claim 32 wherein the cap for the sample reservoir is vented to prevent air locking.

34. The method of claim 32 wherein the cap for the sample reservoir comprises a retentate cup.

35. The method of claim 34 wherein the retentate cup is vented to prevent air locking.

36. The method of claim 35 wherein the retentate cup has ribs molded into its inside surface which are designed to engage the outside surface of the sample reservoir.

37. The method of claim 35 wherein the retentate cup has stop means molded into its inner surface.

38. The method of claim 34 wherein after the retentate volume is obtained in step c, the retentate is recovered by the further steps of:
   (d) removing the filtrate cup containing filtrate from the apparatus:
   (e) inverting the apparatus so that the retentate cup is situated below the sample reservoir;
   (f) centrifuging the apparatus in the inverted orientation to expel a maximal amount of retentate into the retentate cup.

39. The method of claim 38 wherein the step f, the apparatus is centrifuged in a fixed angle rotor.

40. The method of claim 38 wherein in step f, the apparatus is centrifuged in a swinging bucket rotor.

41. The method of claim 38 wherein before the apparatus is centrifuged in step f, the retentate cup is inserted partially into the filtrate cup of step d.

42. The method of claim 41 wherein the retentate cup is inserted partially into the filtrate cup of step d in such a manner that it forms an airtight seal preventing filtrate evaporation.

43. The method of claim 42 further comprising the steps of:
(g) removing the sample reservoir from the retentate cup; and
(h) capping the retentate cup for subsequent storage.

44. The method of claim 38 further comprising the steps of:
(g) removing the sample reservoir from the retentate cup;
(h) inserting the retentate cup partially into the filtrate cup of step d in such a manner that it forms an airtight seal preventing filtrate evaporation; and
(i) capping the retentate cup for subsequent storage.

45. The method of claim 22 wherein after the retentate volume is obtained in step c, the retentate is recovered by the further steps of:
(d) removing the filtrate cup containing filtrate from the apparatus;
(e) capping the sample reservoir with a retentate cup and inverting the apparatus so that the retentate cup is situated below the sample reservoir; and
(f) centrifuging the apparatus in the inverted orientation to expel a maximal amount of retentate into the retentate cup.

46. A method for concentrating macromolecules from a solution without filtering to dryness comprising:
(a) filing the sample reservoir of an apparatus with a macromolecular solution, said apparatus comprising:
a sample reservoir;
a filtrate cup situated below the sample reservoir;
a filter means separating the sample reservoir from the filtrate cup, said filter means comprising:
a semipermeable membrane; and
a support for said membrane, said support having one or more filtrate ducts to allow for passage of filtrate from the membrane into the filtrate cup, said filtrate duct or ducts being located such that when the apparatus is placed in a fixed angle centrifuge rotor in step b, the distance from the outermost edge of the outermost filtrate duct to the centrifugal wall of the sample reservoir is essentially nonvariant with regard to alignment of the apparatus in the rotor and said filtrate duct or ducts being offset sufficiently inward from the edge of the membrane to enable filtration to stop and a concentrated macromolecular final retentate volume to be obtained when the apparatus is used in a fixed angle centrifuge rotor and the retentate meniscus reaches the centrifugal radial level of the outermost edge of the outermost filtrate duct;
means for producing a liquid tight seal between the periphery of the sample reservoir, the membrane, and the membrane support;
means for attaching the sample reservoir to the filter means; and
means for attaching the filter means to the filtrate cup;
(b) placing the apparatus in a fixed angle centrifuge rotor so that during the centrifugation the centrifugal force vector is always at an angle to the membrane surface; and
(c) obtaining a concentrated macromolecular final retentate volume by centrifuging the apparatus until the retentate meniscus reaches the centrifugal radial level of the outermost edge of the outermost filtrate duct and filtration stops.

47. The method of claim 46 wherein the membrane comprises an anisotropic ultrafiltration membrane.

48. The method of claim 46 wherein the filtrate duct comprises a single circular opening.

49. The method of claim 46 wherein the filtrate ducts comprise a series of discontinuous arcs defining an annular slot.

50. The method of claim 46 wherein the membrane support has collection grooves leading to the one or more filtrate ducts which enable the filtrate to flow through the membrane support at a greater speed.

51. The method of claim 46 wherein after the sample reservoir is filled with a macromolecular solution in step a, the sample reservoir is capped.

52. The method of claim 51 wherein the cap for the sample reservoir is vented to prevent air locking.

53. The method of claim 51 wherein the cap for the sample reservoir comprises a retentate cup.

54. The method of claim 53 wherein after the retentate volume is obtained in step c, the retentate is recovered by the further steps of:
(d) removing the filtrate cup containing filtrate from the apparatus:
(e) inverting the apparatus so that the retentate cup is situated below the sample reservoir;
(f) centrifuging the apparatus in the inverted orientation to expel a maximal amount of retentate into the retentate cup.

55. The method of claim 54 further comprising the steps of:
(g) removing the sample reservoir from the retentate cup;
(h) inserting the retentate cup partially into the filtrate cup of step d in such a manner that it forms an airtight seal preventing filtrate evaporation; and
(i) capping the retentate cup for subsequent storage.

56. The method of claim 54 wherein before the apparatus is centrifuged in step f, the retentate cup is inserted partially into the filtrate cup of step d.

57. The method of claim 56 wherein the retentate cup is inserted partially into the filtrate cup of step d in such a manner that it forms an airtight seal preventing filtrate evaporation.

58. The method of claim 57 further comprising the steps of
(g) removing the sample reservoir from the retentate cup; and
(h) capping the retentate cup for subsequent storage.

59. A centrifugal filtration apparatus for the concentration of macromolecules from a solution comprising:
a sample reservoir;
a filtrate cup situated below the sample reservoir;
a filter means separating the sample reservoir from the filtrate cup, said filter means comprising:
a semipermeable membrane; and
a support for said membrane, said support having one or more filtrate ducts to allow for passage of filtrate from the membrane into the filtrate cup, said filtrate duct or ducts being located such that the distance from the outermost edge of the outermost filtrate duct to the centrifugal wall of the sample reservoir is essentially nonvariant with regard to alignment of the apparatus in the rotor and said filtrate duct or ducts being offset sufficiently inward from the edge of the membrane to enable filtration to stop and a concentrated macromolecular final retentate volume to be obtained when the apparatus is used in a centrifuge rotor and the retentate meniscus reaches the centrifugal radial level of the outermost edge of the outermost filtrate duct;

means for providing a liquid tight seal between the periphery of the sample reservoir, the membrane, and the membrane support;

means for attaching the filter means to the filtrate cup; and means for attaching the sample reservoir to the filter means.

60. A method for concentrating macromolecules from a solution without filtering to dryness comprising:
(a) filling the sample reservoir of an apparatus with a macromolecular solution, said apparatus comprising:
a sample reservoir;
a filtrate cup situated below the sample reservoir;
a filter means separating the sample reservoir from the filtrate cup, said filter means comprising:
a semipermeable membrane; and
a support for said membrane, said support having one or more filtrate ducts to allow for passage of filtrate from the membrane into the filtrate cup, said filtrate duct or ducts being offset sufficiently inward from the edge of the membrane to enable filtration to stop and a concentrated macromolecular final retentate volume to be obtained when the apparatus is used in a centrifuge rotor and the retentate meniscus reaches the centrifugal radial level of the outermost edge of the outermost filtrate duct;
means for providing a liquid tight seal between the periphery of the sample reservoir, the membrane, and the membrane support;
means for attaching the filter means to the filtrate cup; and
means for attaching the sample reservoir to the filter means;
(b) placing the apparatus in a centrifuge rotor so that during centrifugation the centrifugal force vector is always at an angle to the membrane surface; and
(c) obtaining a concentrated macromolecular final retentate volume by centrifuging the apparatus until the retentate meniscus reaches the centrifugal radial level of the outermost edge of the outermost filtrate duct and filtration stops.

61. The method of claim 60 wherein after the sample reservoir is filled with a macromolecular solution in step a, the sample reservoir is capped.

62. The method of claim 61 wherein the cap for the sample reservoir comprises a retentate cup.

63. The method of claim 62 wherein after the retentate volume is obtained in step c, the retentate is recovered by the further steps of:
(d) removing the filtrate cup containing filtrate from the apparatus;
(e) inverting the apparatus so that the retentate cup is situated below the sample reservoir;
(f) centrifuging the apparatus in the inverted orientation to expel a maximal amount of retentate into the retentate cup.

64. The method of claim 60 wherein after the retentate volume is obtained in step c, the retentate is recovered by the further steps of:
(d) removing the filtrate cup containing filtrate from the apparatus;
(e) capping the sample reservoir with a retentate cup and inverting the apparatus so that the retentate cup is situated below the sample reservoir; and
(f) centrifuging the apparatus in the inverted orientation to expel a maximal amount of retentate into the retentate cup.

65. A centrifugal filtration apparatus for the concentration of macromolecules from a solution comprising:
a sample reservoir;
a filtrate cup situated below the sample reservoir;
a filter means separating the sample reservoir from the filtrate cup, said filter means comprising:
a semipermeable membrane; and
a support for said membrane, said support having one or more filtrate ducts to allow for passage of filtrate from the membrane into the filtrate cup, said filtrate duct or ducts being offset sufficiently inward from the edge of the membrane to enable filtration to stop and a concentrated macromolecular final retentate volume to be obtained when the apparatus is used in a fixed angle centrifuge rotor and the retentate meniscus reaches the centrifugal radial level of the outermost edge of the outermost filtrate duct;
means for providing a liquid tight seal between the periphery of the sample reservoir, the membrane, and the membrane support;
means for attaching the filter means to the filtrate cup; means for attaching the sample reservoir to the filter means; and
a vented cap for closing the sample reservoir.

66. A centrifugal filtration apparatus for the concentration of macromolecules from a solution comprising:
a sample reservoir;
a filtrate cup situated below the sample reservoir;
a filter means separating the sample reservoir from the filtrate cup, said filter means comprising:
a semipermeable ultrafiltration membrane; and
a support for said membrane, said support having one or more filtrate ducts to allow for passage of filtrate from the membrane into the filtrate cup, said filtrate duct or ducts being offset sufficiently inward from the edge of the membrane to enable filtration to stop and a concentrated macromolecular final retentate volume to be obtained when the apparatus is used in a centrifuge rotor and the retentate meniscus reaches the centrifugal radial level of the outermost edge of the outermost filtrate duct;
means for providing a liquid tight seal between the periphery of the sample reservoir, the membrane, and the membrane support;
means for attaching the filter means to the filtrate cup;
means for attaching the sample reservoir to the filter means; and
a vented cap for closing the sample reservoir.

* * * * *